US012629473B2

(12) United States Patent
Cleveland et al.

(10) Patent No.: US 12,629,473 B2
(45) Date of Patent: May 19, 2026

(54) SYSTEMS AND METHODS FOR PRODUCING MIXTURES

(71) Applicants: Boston Scientific Medical Device Limited, Galway (IE); Boston Scientific Scimed, Inc., Maple Grove, MN (US)

(72) Inventors: Benjamin Cleveland, Bellingham, MA (US); Subodh Morey, Ponda (IN); Nitesh Ghananil Baviskar, Kalyan West (IN); Junaid Mohammed Shaikh, Surat (IN); Richard Earl Graffam, Pelham, NH (US); Joseph Hernandez, Rutland, MA (US); Christopher Watson, Lincoln, MA (US); Kolbein Kolste, Acton, MA (US); Nabarun Bhowmick, Kolkata (IN); Mihir Sukhatme, Thane (IN); Nachiket Gole, Pune (IN); Rajivkumar Singh, Thane (IN)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 776 days.

(21) Appl. No.: 17/970,763

(22) Filed: Oct. 21, 2022

(65) Prior Publication Data

US 2023/0191028 A1     Jun. 22, 2023

Related U.S. Application Data

(60) Provisional application No. 63/262,934, filed on Oct. 22, 2021.

(51) Int. Cl.
| | | |
|---|---|---|
| *A61M 5/19* | (2006.01) | |
| *A61J 1/20* | (2006.01) | |
| *A61M 5/24* | (2006.01) | |

(52) U.S. Cl.
CPC ................ *A61M 5/19* (2013.01); *A61J 1/201* (2015.05); *A61J 1/2089* (2013.01); *A61J 1/2096* (2013.01); *A61M 5/2448* (2013.01)

(58) Field of Classification Search
CPC .. A61M 5/19; A61M 5/2448; A61M 5/31596; A61M 39/22; A61J 1/201; A61J 1/2089; A61J 1/2096
See application file for complete search history.

(56) References Cited

U.S. PATENT DOCUMENTS

| | | | |
|---|---|---|---|
| 4,735,616 A | | 4/1988 | Eibl et al. |
| 5,240,146 A | * | 8/1993 | Smedley ............... A61M 5/315 |
| | | | 604/82 |

(Continued)

FOREIGN PATENT DOCUMENTS

WO       2017012889 A1      1/2017

OTHER PUBLICATIONS

International Search Report and Written Opinion in International Application No. PCT/US2022/047369, dated Jan. 19, 2023 (14 pages).

*Primary Examiner* — Theodore J Stigell
(74) *Attorney, Agent, or Firm* — Bookoff McAndrews, PLLC

(57) ABSTRACT

The system can include a multi-lumen chamber can removably connected to and in fluid communication with a proximal end of a mixing lumen and include a first lumen aligned with a second lumen. The first lumen can be configured to include a first constituent in a first cavity. A first plunger can be internally positioned within the first lumen to control flow of the first constituent from the first cavity into the mixing (Continued)

lumen. The first cavity can terminate in a first port in fluid communication with the proximal end of the mixing lumen. The second lumen can be configured to include a second constituent. A second plunger can be internally positioned within the second lumen. The second lumen can terminate in a second port adjacent the first port and in fluid communication with the proximal end of the mixing lumen.

4 Claims, 12 Drawing Sheets

(56)                    References Cited

U.S. PATENT DOCUMENTS

| | | |
|---|---|---|
| 6,283,946 B1 | 9/2001 | Fischer |
| 2015/0250463 A1 | 9/2015 | Jamiolkowski et al. |
| 2017/0304553 A1 | 10/2017 | Bender et al. |

\* cited by examiner

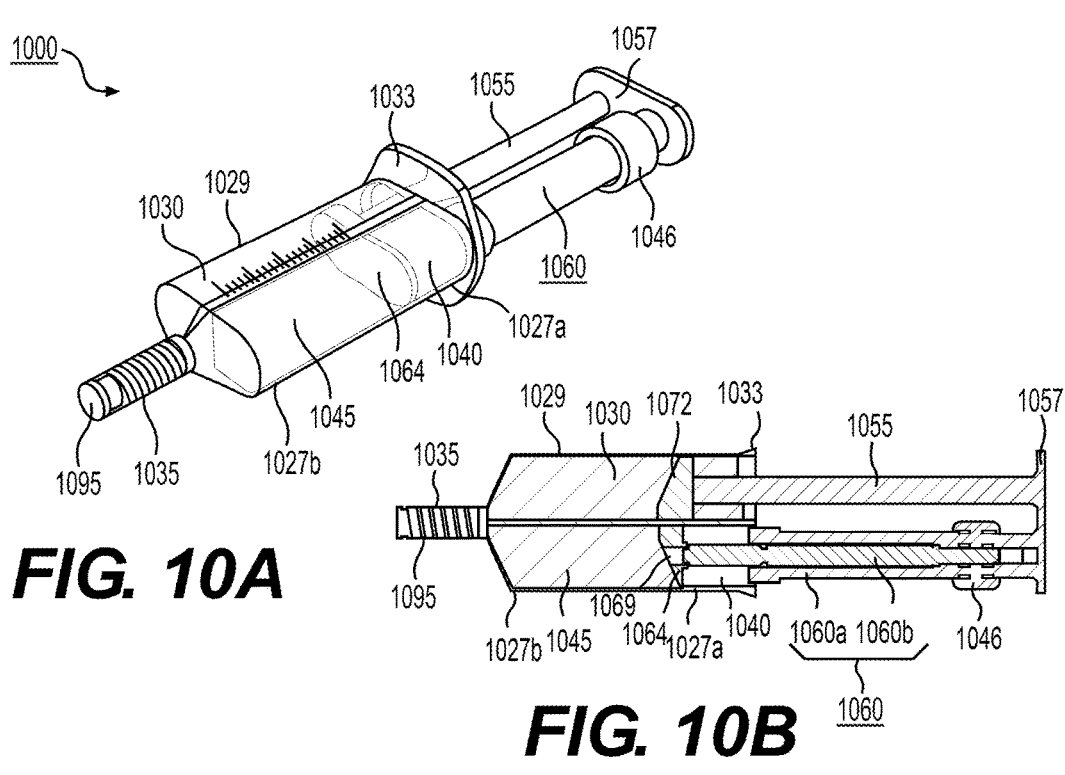
FIG. 10A
FIG. 10B
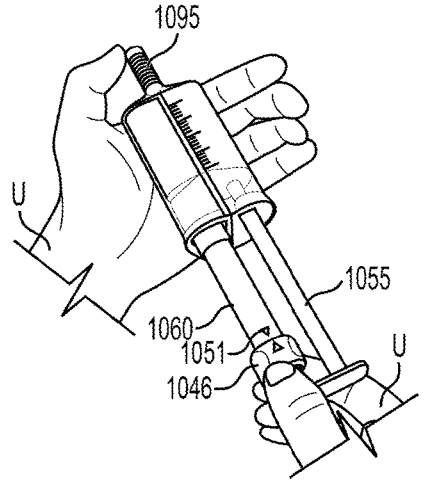
FIG. 10C
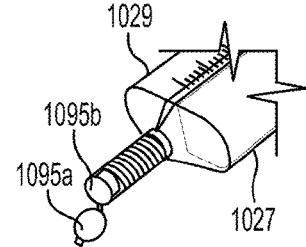
FIG. 10D
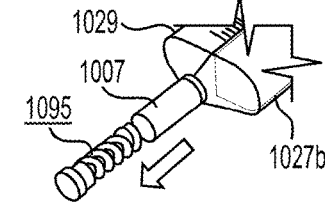
FIG. 10E

_1200_

opening, by the first plunger, a barrier between proximal and distal portions within the first lumen thereby mixing the first constituent with another constituent in a first state to form a first mixture
_1210_ moving the second plunger causing the first constituent and the second constituent to be delivered through the first and second ports and mixed together within the mixing lumen to form the mixture
_1220_

_FIG. 12_

SYSTEMS AND METHODS FOR PRODUCING MIXTURES

CROSS-REFERENCE TO RELATED APPLICATIONS

This patent application claims the benefit of priority under 35 U.S.C. § 119 to U.S. Provisional Patent Application No. 63/262,934, filed Oct. 22, 2021, which is herein incorporated by reference in its entirety.

FIELD

The present disclosure relates generally to compositions for injection to a patient, methods of preparation and use thereof, and devices comprising such compositions.

BACKGROUND

Numerous men are diagnosed with prostate cancer each year. Traditionally, treatment options include interstitial implant therapy, surgery, and external beam radiotherapy. While the best treatment is still debatable, side effects of treating prostate cancer have become less toxic with implant therapy and radiotherapy.

Since the conception of conformal radiotherapy, physicians have paid attention to the delivered dose to the target and surrounding tissues. Investigators have been able to correlate side effects to the amount of tissue receiving a certain radiation dose. And yet, time, distance, and shielding affect the dose that is delivered. The less time an area is exposed to radiation, the less dose delivered. The greater the distance from the radiation, the less dose delivered.

Current systems provide filler material to treatment sites to decrease the radiation dose to the rectum during radiotherapy for prostate cancer. However, the system that mixes the filler material in vitro includes numerous subcomponents, is complex to assemble, and rife with filler mixing errors prior to delivery within a patient at a treatment site. During the foregoing procedures, such errors and mishaps lead unnecessarily to patient risk, increased procedure time, and increased procedure costs. The solution of this disclosure resolves these and other issues of the art.

SUMMARY

In accordance with certain aspects of the present disclosure, a system is disclosed for producing a mixture to deliver to a treatment site. The system can include a mixing lumen attachable to a proximal end of a delivery system. A multi-lumen chamber can removably connected to and in fluid communication with a proximal end of the mixing lumen and include a first lumen aligned with a second lumen. The first lumen can be configured to include a first constituent in a first cavity. A first plunger can be internally positioned within the first lumen to control flow of the first constituent from the first cavity into the mixing lumen. The first cavity can terminate in a first port in fluid communication with the proximal end of the mixing lumen. The second lumen can be configured to include a second constituent. A second plunger can be internally positioned within the second lumen. The second lumen can terminate in a second port adjacent the first port and in fluid communication with the proximal end of the mixing lumen. Distally moving the second plunger can cause the first constituent and the second constituent to be delivered through the first and second ports and mixed together within the mixing lumen to form the mixture.

In accordance with certain aspects of the present disclosure, the mixing lumen is in a connector including a distal end and a proximal end, the distal end of the mixing lumen being attachable to a proximal end of a needle.

In accordance with certain aspects of the present disclosure, the connector including a hole sized to receive an insert with a plurality of channels configured to control fluid flow within the mixing lumen and out of the first and second lumens. The insert can be substantially cylindrical with the plurality of channels being holes selectively positioned throughout the insert.

In accordance with certain aspects of the present disclosure, the connector can include a hole sized to receive an insert with a plurality of channels configured to control fluid flow within the mixing lumen and out of the first and second lumens. Rotating the insert between one or more orientations with respect to the hole and the mixing lumen adjusts a flow setting of the system.

In accordance with certain aspects of the present disclosure, the connector including a hole sized to receive an insert with a plurality of channels configured to control fluid flow within the mixing lumen and out of the first and second lumens. Moving the insert into and out of the hole between one or more positions with respect to the hole and the mixing lumen adjusts a flow setting of the system.

In accordance with certain aspects of the present disclosure, a link can removably connect the proximal ends of the first and second plunger to each other. Upon connecting the link with proximal ends of the first and second plungers, distally moving the second plunger causes the first constituent and the second constituent to be delivered through the first and second ports and mixed together within the mixing lumen to form the mixture.

In accordance with certain aspects of the present disclosure, the link is a separate plate slidably connected to the proximal ends of the first and second plungers.

In accordance with certain aspects of the present disclosure, the link includes one or more connectors to securely engage with each of the proximal ends of the first and second plungers.

In accordance with certain aspects of the present disclosure, the link integrally formed with a flange of the proximal end of the second plunger, the link including a receiver so that rotating the second plunger causes the receiver of the link to contact and securely engage with the proximal end of the first plunger.

In accordance with certain aspects of the present disclosure, the first cavity is configured to removably connect to a vial including a third constituent. The third constituent from the vial can be loadable through a distal end of the first cavity to form a first mixture. The first mixture can be the first constituent. Upon forming the first mixture, the first cavity is configured to be detached from the vial and removably connected to the mixing lumen.

In accordance with certain aspects of the present disclosure, the first cavity can include a distal syringe including a hydrophilic polymer with a distal portion being narrower than a proximal portion. A proximal syringe can include a diluent solution insertable and be concentric with the distal syringe. The proximal syringe can include a first rod coupled with the first plunger. A distal portion can be wider than a proximal portion. Distally moving the first plunger can cause an opening to form between the proximal portion of the distal syringe and the distal portion of the proximal syringe so that the diluent and the hydrophilic form a first mixture, the first mixture being the first constituent.

In accordance with certain aspects of the present disclosure, the first cavity includes a distal syringe including a diluent solution. The first plunger being insertable within the distal syringe and including a hydrophilic polymer within a vial housing of the first plunger. A seal can separate the diluent syringe and a distal end of the first plunger. Pressing the distal end of the first plunger can cause the seal to open and release the hydrophilic polymer with the diluent solution to form a first mixture, the first mixture being the first constituent.

In accordance with certain aspects of the present disclosure, the first cavity can include an external fluid port configured to receive a vial including a hydrophilic polymer. The vial can include an actuator so that actuating the actuator when the vial is connected to the external fluid port causes a hydrophilic polymer to be released from the vial and mix with the first constituent of the first cavity.

In accordance with certain aspects of the present disclosure, a first rod is coupled to the first plunger and includes a rotating knob between the first plunger of the first rod and a flange of the first rod.

In accordance with certain aspects of the present disclosure, the first plunger can include an internal cavity including hydrophilic polymer, wherein rotating the rotating knob causes the hydrophilic polymer to be released from the internal cavity of the first plunger and mix with a diluent distal thereof in the first cavity to form a first mixture, the first mixture being the first constituent.

In accordance with certain aspects of the present disclosure, a method is disclosed for producing a mixture with a mixing system to deliver to a treatment site. The mixing system can be any of this disclosure, including one having a multi-lumen chamber removably connected to and in fluid communication with a proximal end of a mixing lumen. A first lumen can be aligned a second lumen. The first lumen can be configured to include a first constituent in a first cavity. A first plunger can be internally positioned within the first lumen to control flow of the first constituent from the first cavity into the mixing lumen. The first cavity can terminate in a first port in fluid communication with the mixing lumen. The second lumen can be configured to include a second constituent. A second plunger can be internally positioned within the second lumen. The second lumen can terminate in a second port adjacent the first port and in fluid communication with the mixing lumen. The method can include opening, by the first plunger, a barrier between proximal and distal portions within the first lumen thereby mixing the first constituent with another constituent in a first state to form a first mixture. The method can include moving the second plunger causing the first constituent and the second constituent to be delivered through the first and second ports and mixed together within the mixing lumen to form the mixture.

In accordance with certain aspects of the present disclosure, the method can include removably connecting a link to the proximal ends of the first and second plungers; and wherein upon connecting the link with proximal ends of the first and second plungers, the step of moving the second plunger causes at least the first constituent and the second constituent to be delivered through the first and second ports, mixed together within the mixing lumen to form the mixture, and be delivered to the treatment site.

In accordance with certain aspects of the present disclosure, the link is a separate plate slidably connected to proximal ends of the first and second plungers.

In accordance with certain aspects of the present disclosure, the link includes one or more connectors to securely engage with each of the proximal ends of the first and second plungers.

In accordance with certain aspects of the present disclosure, the link is integrally formed with a flange of the proximal end of a second plunger rod coupled to the second plunger, the link including a receiver so that rotating the second plunger rod causes the receiver of the link to contact and securely engage with the proximal end of the first plunger.

In accordance with certain aspects of the present disclosure, the method can include removably connecting the first cavity of the lumen to the first plunger and the mixing lumen; removably connecting the first cavity to a vial including the first constituent or the other constituent; loading, from the vial, the first constituent or the other constituent through a distal end of the first cavity to form the first mixture; and upon forming the first mixture, detaching the vial form the cavity.

In accordance with certain aspects of the present disclosure, the first cavity can include a distal syringe including the first constituent or the other constituent with a distal portion being narrower than a proximal portion. A proximal syringe can contain the other of the first constituent and the other constituent and be insertable and concentric with the distal syringe. The proximal syringe including the first plunger, and a distal portion wider than a proximal portion. The method can include moving the first plunger thereby causing an opening to form between the proximal portion of the distal syringe and the distal portion of the proximal syringe so that the first constituent and the other constituent form the first mixture.

In accordance with certain aspects of the present disclosure, the first cavity includes a distal syringe including the first constituent or the other constituent. The method can include inserting the first plunger within the distal syringe; containing the other of the first constituent and the other constituent within a vial housing of the first plunger; separating, by a seal, the distal syringe and a distal end of the first plunger; and pressing the distal end of the first plunger thereby causing the seal to open and release the first constituent and the other constituent to form the first mixture.

In accordance with certain aspects of the present disclosure, the first cavity can include an external fluid port configured to receive a vial including the first constituent or the other constituent. The vial can include an actuator. The method can include actuating the actuator when the vial is connected to the external fluid port causing the other of the first constituent and the other constituent to be released from the vial and mix to form the first mixture in the first cavity.

In accordance with certain aspects of the present disclosure, the first constituent is a diluent and the third constituent is an accelerator, and wherein the first mixture is a precursor fluid solution.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE FIGURES

The accompanying drawings, which are incorporated in and constitute a part of this specification, illustrate various exemplary aspects of the disclosure, and together with the description serve to explain the principles of the present disclosure.

FIG. 10A depicts a perspective view of aspects of an example mixing system, in accordance with certain aspects of the present disclosure.

FIG. 10B depicts a partial side, cross-sectional view of aspects of the example mixing system of FIG. 10A, in accordance with certain aspects of the present disclosure.

FIG. 10C depicts a partial side, cross-sectional view of aspects of the example mixing system of FIGS. 10A-10B, in accordance with certain aspects of the present disclosure.

FIG. 10D depicts a perspective view of aspects of the example mixing system of FIGS. 10A-10C, in accordance with certain aspects of the present disclosure.

FIG. 10E depicts a close-up, partial perspective view of aspects of the example mixing system of FIGS. 10A-10D, in accordance with certain aspects of the present disclosure.

FIG. 12 depicts a flow diagram of a method of using a mixing system according to certain aspects of this disclosure.

DETAILED DESCRIPTION

Figure 1A:
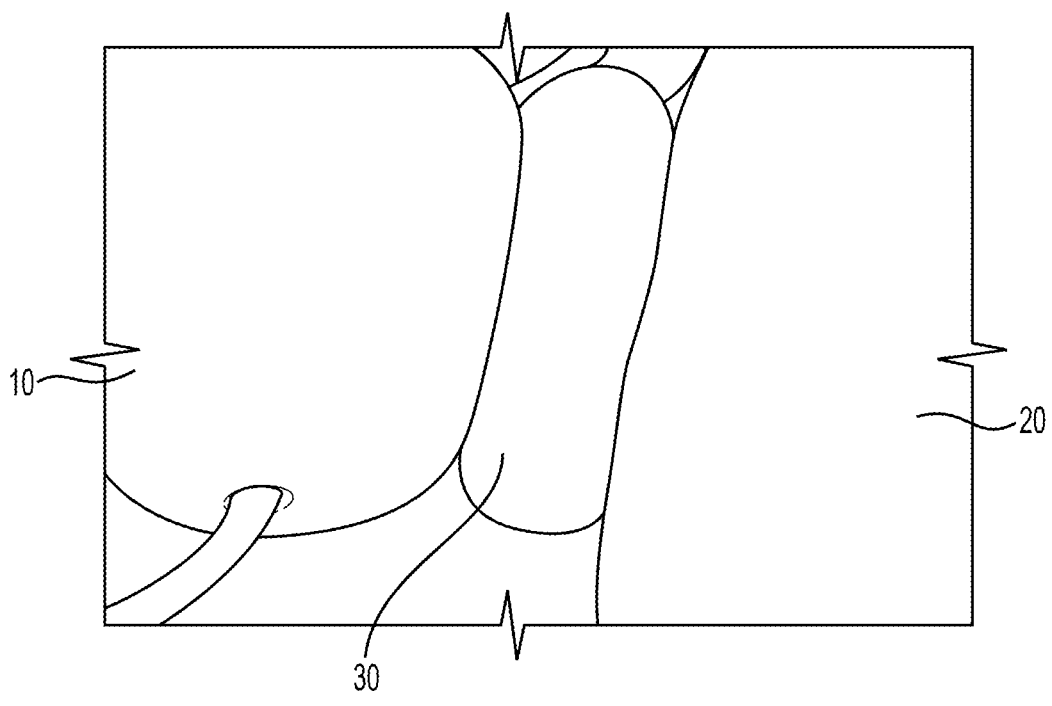
FIGS. 1A-1B depict the prostate, rectum, and Denonvilliers' space between the prostate and rectum.

Particular aspects of the present disclosure are described in greater detail below. The terms and definitions provided herein control, if in conflict with terms and/or definitions incorporated by reference.

Particular aspects of the present disclosure may repeat reference numerals and/or letters in the various examples. This repetition is for the purpose of simplicity and clarity and does not in itself dictate a relationship between the various embodiments and/or configurations discussed. Different embodiments may have different advantages, and no particular advantage is necessarily required of any embodiment.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise.

As used herein, "approximately" and "about" refer to being nearly the same as a referenced number or value. As used herein, the terms "approximately" and "about" should be understood to encompass ±10% of a specified amount or value (e.g., "about 90%" can refer to the range of values from 81% to 99%).

As used herein, "operator" can include a doctor, surgeon, or any other individual or delivery instrumentation associated with delivery or use of a mixing system as such systems are described throughout this disclosure.

The compositions herein may be used in various medical procedures, including but not limited to injected to create additional space between the rectum and prostate during treatment, for example in the Denonvilliers' space, thereby reducing rectal radiation dose and associated side effects. Certain embodiments of the disclosure include placing a filler between the radiation target tissue and other tissues. The filler can be a gel composition that increases the distance between the target tissue and other tissues so that the other tissues receive less radiation.

It is understood that "Denonvilliers' space" is a region located between the rectum and prostate. Certain embodiments provide a method of displacing a tissue to protect the tissue against the effects of a treatment involving radiation or cryotherapy. One embodiment involves using a filler mixed by a mixing system of this disclosure to displace the tissue relative to a tissue that is to receive the treatment. Another embodiment involves introducing a filler mixed by a mixing system of this disclosure to displace a first tissue and radiating a second tissue, particularly a second tissue that is close to the first tissue. In another embodiment, the method includes the steps of injecting a filler into a space between tissues; and may further include irradiating one of the tissues so that the other tissue receives less radiation than it would have in the absence of the filler.

Certain embodiments also provide methods for treating a tissue of a body by radiation. In one embodiment, the method includes the steps of injecting an effective amount of a filler into a space between a first tissue (e.g., prostate) of a body and a second tissue (e.g., rectum), which can be a critically sensitive organ; and treating the first tissue by radiation whereby the filler within the space reduces passage of radiation into the second tissue. Tissue is a broad term that encompasses a portion of a body: for example, a group of cells, a group of cells and interstitial matter, an organ, a portion of an organ, or an anatomical portion of a body, e.g., a rectum, ovary, prostate, nerve, cartilage, bone, brain, or portion thereof.

The gel of the filler can include polymeric materials which are capable of forming a hydrogel may be utilized. In one embodiment, the polymer forms a hydrogel within the body. A hydrogel is defined as a substance formed when an organic polymer (natural or synthetic) is cross-linked via covalent, ionic, or hydrogen bonds to create a three-dimensional open-lattice structure which entraps water molecules to a gel. Naturally occurring and synthetic hydrogel forming polymers, polymer mixtures, and copolymers may be utilized as hydrogel precursors.

In some aspects, the hydrogel can be formed by a composition formed by mixing constituents together (E.g., accelerant fluid, diluent, and PEG together) and may comprise one or more polysaccharide compounds or a salt thereof. For example, the composition may include a cellulose compound such as carboxymethyl cellulose (CMC) or salt thereof (e.g., CMC) sodium, xanthan gum, alginate or a salt thereof (e.g., calcium alginate, such as Ca-alginate beads), chitosan, and/or hyaluronic acid. In some examples, the composition may comprise a mixture of hyaluronic acid and CMC, and/or may be cross-linked with a suitable crosslinking compound, such as butanediol diglycidyl ether (BDDE). In some aspects, the polysaccharide may be a homopolysaccharide or a heteropolysaccharide The present disclosure also provides mixing systems to form the gel composition and corresponding medical devices for use and/or delivery to a treatment site of a patient. According to some aspects of the present disclosure, the mixing system may include a plurality of reservoirs with respective lumens. Collectively, the lumens therein may serve as a container for constituents to mix the gel composition of this disclosure. Suitable reservoirs may include, for example, syringes (e.g., a syringe barrel compatible with a manual or automatic injection system) and other fluid containers configured for use with a suitable injection needle. Exemplary materials suitable for the reservoir include, but are not limited to, cyclic olefin polymer, polypropylene, polycarbonate, polyvinyl chloride, and glass. In some aspects, one of these materials (e.g., cyclic olefin copolymer specifically) can have a coating applied to it, such as $SiO_2$), which is advantageous so the coating can perform as a primary oxygen barrier, behave as a glass-like layer, and can be applied using a vapor deposition process.

According to some aspects of the present disclosure, the compositions may include at least one accelerant (e.g., an activating agent) combined with a precursor mixed from a diluent (e.g., mostly water) and polyethylene glycol (PEG). In some examples, the composition may be or include a gel with a desired gel strength and/or viscosity, such as a biocompatible gel suitable for injection (e.g., through a needle).

The hydrophilic polymer can be any gelling agent(s), including natural ones or synthetic in origin, and may be anionic, cationic, or neutral. Non-limiting examples of the gelling agents include polysaccharides such as gellan gum, xanthan gum, gum arabic, guar gum, locust bean gum, alginate, and carrageenans.

The concentrations of gelling agent(s) in the composition described in this disclosure may range from about 0.01% to about 2.0% by weight with respect to the total weight of the composition, such as from about 0.02% to about 1.5%, from about 0.05% to about 1.0%, from about 0.05% to about 0.50%, from 0.05% to about 0.15%, from about 0.10% to about 0.20%, from about 0.15% to about 0.25%, from about 0.20% to about 0.30%, from about 0.25% to about 0.35%, from about 0.30% to about 0.40%, from about 0.35% to about 0.45%, from about 0.40% to about 0.50%, from about 0.1% to about 0.5%, or from about 0.1% to about 0.15% by weight with respect to the total weight of the composition. In at least one example, the total concentration of the gelling agent(s) in the composition may range from about 0.05% to about 0.5% by weight with respect to the total weight of the composition.

In some examples, the composition may have a viscosity ranging from about 0.001 Pa·scal-second (Pa·s) to about 0.100 Pa·s at a shear rate of 130 s$^{-1}$, such as, e.g., from about 0.005 Pa·s to about 0.050 Pa·s, from about 0.010 Pa·s to about 0.050 Pa·s, from about 0.010 Pa·s to about 0.030 Pa·s, from about 0.010 Pa·s to about 0.020 Pa·s, from about 0.020 Pa·s to about 0.030 Pa·s, or from about 0.020 Pa·s to about 0.040 Pa·s at a shear rate of 130 s$^{-1}$. Thus, for example, the composition may be or comprise a gel having a viscosity of about 0.005 Pa·s, about 0.006 Pa·s, 0.008 Pa·s, about 0.010 Pa·s, about 0.011 Pa·s, about 0.012 Pa·s, about 0.013 Pa·s, about 0.014 Pa·s, about 0.015 Pa·s, about 0.016 Pa·s, about 0.017 Pa·s, about 0.018 Pa·s, about 0.019 Pa·s, about 0.020 Pa·s, about 0.022 Pa·s, about 0.024 Pa·s, about 0.026 Pa·s, about 0.028 Pa·s, about 0.030 Pa·s, about 0.032 Pa·s, about 0.034 Pa·s, about 0.036 Pa·s, about 0.038 Pa·s, about 0.040 Pa·s, about 0.042 Pa·s, about 0.044 Pa·s, about 0.046 Pa·s, about 0.048 Pa·s, or about 0.050 Pa·s at a shear rate of 130 $s^{-1}$. In at least one example, the composition may have a viscosity greater than 0.0050 Pa·s at a shear rate of 130 $s^{-1}$, e.g., a viscosity ranging from about 0.005 Pa·s to about 0.050 Pa·s, at a shear rate of 130 $s^{-1}$. In at least one example, the composition may have a viscosity greater than 0.010 Pa·s at a shear rate of 130 $s^{-1}$, e.g., a viscosity ranging from about 0.010 Pa·s to about 0.030 Pa·s, at a shear rate of 130 $s^{-1}$.

Alternatively or additionally, the composition may have a viscosity ranging from about 0.001 Pa·s to about 0.050 Pa·s at a shear rate of 768 $s^{-1}$, such as, e.g., from about 0.002 Pa·s to about 0.030 Pa·s, from about 0.003 Pa·s to about 0.020 Pa·s, from about 0.004 Pa·s to about 0.010 Pa·s, from about 0.004 Pa·s to about 0.006 Pa·s, from about 0.005 Pa·s to about 0.007 Pa·s, from about 0.006 Pa·s to about 0.008 Pa·s, from about 0.007 Pa·s to about 0.009 Pa·s, or from about 0.008 Pa·s to about 0.01 Pa·s at a shear rate of 768 $s^{-1}$. Thus, for example, the composition may be or comprise a gel having a viscosity of about 0.003 Pa·s, about 0.004 Pa·s, about 0.005 Pa·s, about 0.006 Pa·s, about 0.007 Pa·s, about 0.008 Pa·s, about 0.009 Pa·s, or about 0.010 Pa·s at a shear rate of 768 $s^{-1}$. In at least one example, the composition may have a viscosity less than 0.010 Pa·s at a shear rate of 768 $s^{-1}$, e.g., a viscosity ranging from about 0.005 Pa·s to about 0.009 Pa·s at a shear rate of 768 $s^{-1}$. In at least one example, the composition may have a viscosity ranging from about 0.004 Pa·s to about 0.010 Pa·s at a shear rate of 768 $s^{-1}$. Further, for example, the composition may have a viscosity ranging from about 0.010 Pa·s to about 0.030 Pa·s, e.g., about 0.017 Pa·s at a shear rate of 130 $s^{-1}$ and a viscosity ranging from about 0.004 Pa·s to about 0.010 Pa·s, e.g., about 0.007 Pa·s, at a shear rate of 768 $s^{-1}$.

The mixing system herein may include or be removably connected to one or more needles. In some examples, the needle may be a hypodermic needle, and may range from a size of 7 gauge (4.57 mm outer diameter (OD), 3.81 mm inner diameter (ID)) to 33-gauge (0.18 mm OD, 0.08 mm ID), e.g., a size of 16 gauge (1.65 mm OD, 1.19 mm ID), 18 gauge, 21 gauge (0.82 mm OD, 0.51 mm ID), 22 gauge (0.72 mm OD, 0.41 mm ID), 23 gauge (0.64 mm OD, 0.33 ID), or 24 gauge (0.57 mm OD, 0.31 mm ID). Exemplary materials for the needle include, but are not limited to, metals and metal alloys, such as stainless steel and Nitinol, and polymers. The distal tip of the needle may be sharpened, and may have a beveled shape. The proximal end of the needle may include a suitable fitting/adaptor (e.g., a Luer adapter) for engagement with a syringe or other reservoir. In some examples, the needle may include an elongated tube or catheter between the needle tip and the proximal fitting/adapter.

According to some aspects of the present disclosure, the filler compositions herein, e.g., the compositions prepared by the methods herein may have sufficient strength, e.g., gel strength, to withstand the forces and thus minimizing the effects of the forces on the continuity of the three-dimensional gel network. In the meantime, the composition with sufficient strength may have a viscosity suitable for injection, e.g., a viscosity that does not render the composition stuck in the reservoir(s), delivery lumen, or a needle connected therewith.

According to some aspects of the present disclosure, the composition may maintain its three-dimensional structure until the gel is injected through a needle, whereupon the structure may form fragments of the original continuous, three-dimensional network. Those gel fragments may have a diameter corresponding to the diameter of the injection needle, such that the fragments are as large as possible in-vivo to retain as much of the three-dimensional structure of the gel as possible. Injection of these larger-sized particles or fragments is believed to increase the amount of time the gel remains within the tissue.

The amount of force required to move the composition through a needle aperture (generally described as "peak load" force) may depend on the viscosity of the composition, the dimensions of the needle (inner diameter, outer diameter, and/or length), and/or the material(s) from which the needle is formed. For example, a greater amount of force may be applied to inject the composition through a 33-gauge needle in comparison to a 7-gauge needle. Additional factors that may affect the amount of force applied to inject the composition may include the dimensions of a catheter (inner diameter, outer diameter, and/or length) connecting the mixing system to the needle. Suitable peak loads for injection with one or two hands may range from about 5 lbf to about 25 lbf, such as from about 10 lbf to about 20 lbf, e.g., about 15 lbf. The loads measured for a given gel concentration may vary for different needles and flow rates.

According to some aspects of the present disclosure, the size of the needle may be chosen based on the viscosity and/or components of the composition, or vice versa. According to some aspects of the present disclosure, the size of the needle may be 23 gauge or 25 gauge. In some cases, a larger size of 18 gauge, 20 gauge, 21 gauge, or 22 gauge may be used to inject the compositions herein.

According to some aspects of the present disclosure, the mixing system of this disclosure can be included in a kit for introducing a filler into a patient, whereby the filler can include any of the gel compositions of this disclosure. Kits or systems for mixing a gel composition of this disclosure, such as hydrogels, may be prepared so that the precursor(s) and any related activating agent(s) are stored in the kit with diluents as may be needed. Applicators may be used in combination with the same. The kits can be manufactured using medically acceptable conditions and contain components that have sterility, purity and preparation that is pharmaceutically acceptable. Solvents/solutions may be provided in the kit or separately. The kit may include syringes and/or needles for mixing and/or delivery. The kit or system may comprise components set forth herein.

During some examples of use, once saline has been injected to the treatment site, a mixing system can be connected to a needle (e.g., an 18-gauge spinal needle) to then inject a 5-10 mm layer of filler (e.g., gel composition) along the posterior wall of the prostate between the prostate and rectum. Once the filler has been injected into the space between the rectum and prostate, ultrasound images can be obtained.

Figure 1B:
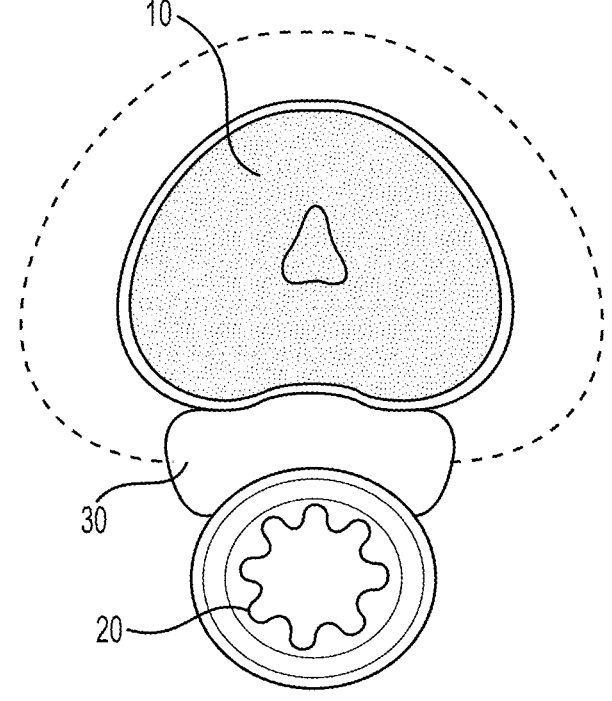

Turning to the drawings, FIG. 1A is a perspective view and FIG. 1B is a partial cross-section view illustrating example filler 30, in the form of a gel composition having been delivered by the mixing system of this disclosure between rectum 20 and prostate 10 of a patient in Denonvilliers' space.

Figure 2:
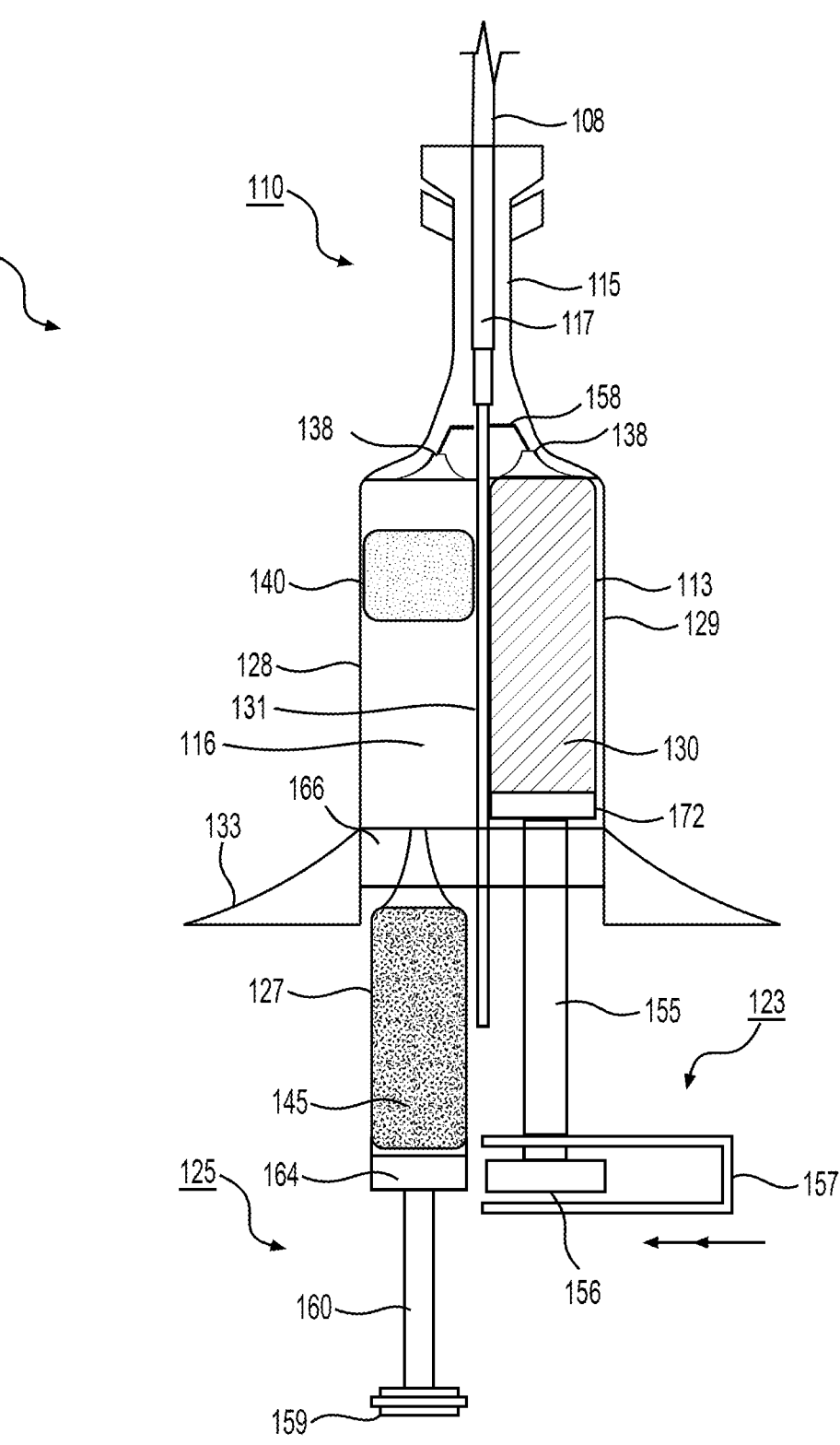
FIG. 2 shows a side plan view of an exemplary mixing system in accordance with certain aspects of the present disclosure.

FIG. 2 shows a side plan view of an exemplary mixing system 100 in accordance with certain aspects of the present disclosure. System 100 can be used for mixing a gel composition for use as filler 30. While not shown, during use it is contemplated that a needle 108 of can be in position at a treatment site of a patient so that filler 30 from system 100 can be delivered to the treatment site through the needle 108. The system 100 can be packaged in a kit that can include a needle assembly 110 with a needle 108 attachable to a distal end of system 100 at a connector 115. Needle assembly 110 can include needle 108, which can be any needle of this disclosure suitable for hydrodissection as well as delivering filler 30 (e.g., the gel composition) to the treatment site. A proximal end of needle 108 can be connected to a distal end of connector 115. Connector 115 can include a central lumen 117 running therethrough.

System 100 can include a multi-lumen chamber formed by a receiver 128 that can receive a first syringe 125 and a second syringe 123. Receiver 128 can include an open, proximal end through which syringes 125, 123 can be inserted. Distal ends of receiver 128 can include plurality of smaller openings configured to include or otherwise receive ports 138 in fluid communication with distal ends of syringes 123, 125. Tubes 158 (e.g., hypotubes) can provide a fluid path between ports 138 and lumen 117. When ports 138 are in fluid communication with respective syringes 123, 125 and tubes 158, the fluid path therebetween can permit egress of fluids from respective lumens 127, 129 into connector 115. Receiver 128 can be divided by divider 131 to form portions 116, 113. Portion 116 can be a cavity that terminates in or is otherwise in fluid communication with one of ports 138. Portion 116 can be sized to snuggly receive syringe 125 and portion 113 can be sized to receive syringe 123. Prior to loading syringe 125 in portion 116, constituent 140 (e.g., an activating agent, such as PEG or any other agent mixable with constituent 145 to intermix and form precursor 145') can be present in portion 116. As used herein, the term "fluid" is defined broadly and can include liquids, gels and particulate matter such as granules, pellets, or powders, or any combination of liquids, gels, oils, and/or particulate matter (e.g., granules, pellets, or powders).

Figure 3B:
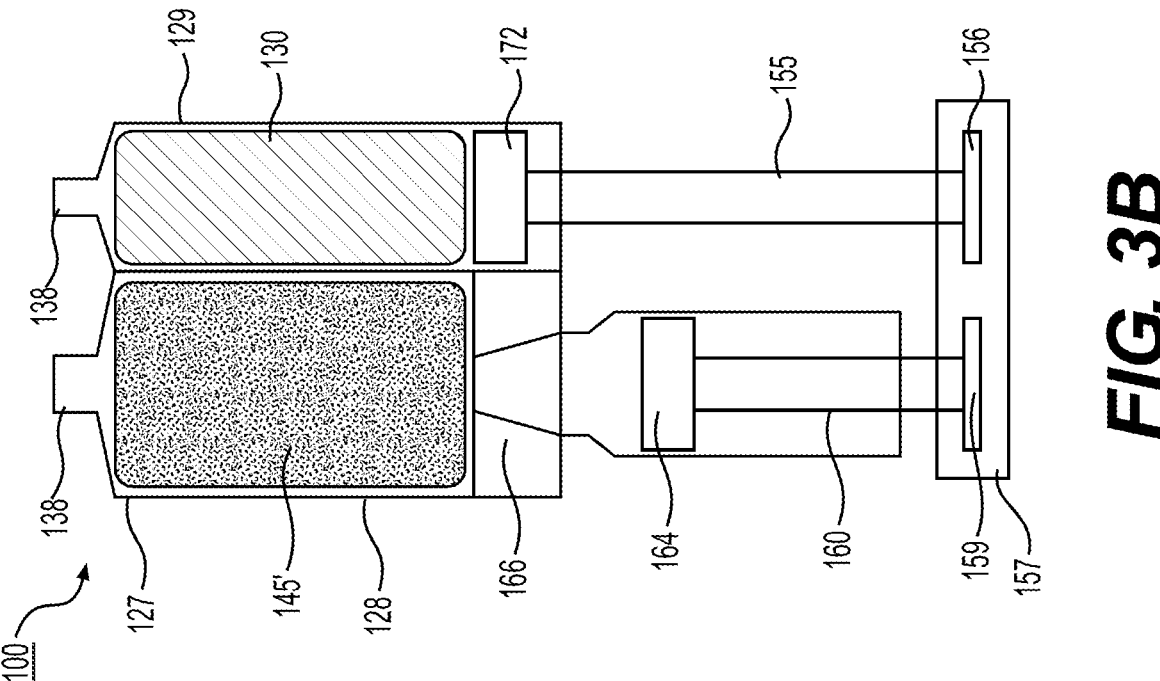
FIG. 3B depicts an example step in a method using the example mixing system of FIG. 2, in accordance with certain aspects of the present disclosure.
Figure 3A:
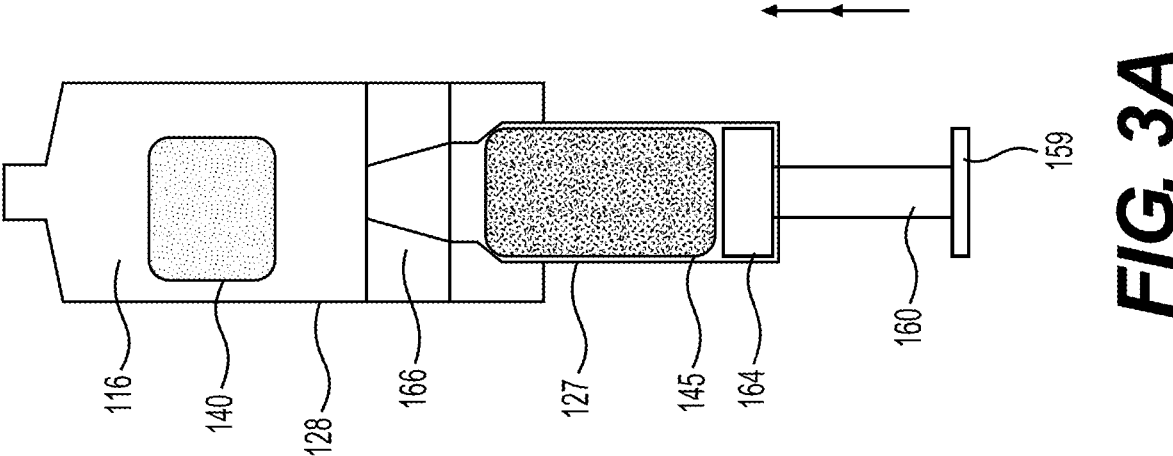
FIG. 3A depicts an example step in a method using the example mixing system of FIG. 2, in accordance with certain aspects of the present disclosure.

Syringe 125 can include a first lumen 127 with plunger rod 160 and corresponding flange 159. A first plunger stopper 164 located at a distal end of a first plunger rod 160. Rod 160 can be advanced by flange 159 positioned on a proximal end of rod 160. Constituent(s) of lumen 127 can be a constituent 145 (e.g., a fluid such as diluent). Once syringe 125 is assembled with receiver 128, distally moving rod 160 can cause stopper 164 to advance constituent 145 so as to open a barrier 166 of portion 116 thereby allowing constituents 140, 145 to intermix and form precursor 145' in portion 116. In FIG. 3A, a side plan view of rod 160 is shown beginning to advance distally so as to initiate mixing between constituents 140, 145. The diluent of either constituent 140, 145 can be a branched polymer having a plurality of succinimidyl termini dissolved in a low pH (4.0) containing a low molecular weight precursor comprising nucleophiles, though other diluent fluid solutions are contemplated within the scope of this disclosure. Barrier 166 can be a membrane having a one-way valve or a floating plunger stopper capable of being toggled when activated by pressure so as to allow the fluid of the lumen to pass thereby.

Syringe 123 can include a second lumen 129 with plunger rod 155 and corresponding flange 156. A distal end of rod 155 can include a stopper 172. Lumen 129 can include one or more constituents 130 therein (e.g., (e.g., accelerant). When assembled in receiver 128, lumens 127, 129 can be oriented parallel with the other, running side-by-side. A flange link 157 can be included with system 100 that is configured so that a user can link flanges 156 and 159 together. Link 157 can be a substrate, a plate, or planar member with notches or openings selectively positioned so that a user can slide link 157 around rods 155, 160 and couple with flanges 156, 159, as shown in FIG. 3B. Link 157 can include one or more connectors to securely engage with flanges 156, 159 and/or rods 155, 160 (e.g., magnetic connectors, snap fit connectors, hook-and-loop fasteners, etc.).

Once coupled by link 157, a user can advance flanges 156, 159 together so as to drive rods 155, 160 proximally or distally and urge fluids from each syringe 123, 125 through ports 138, tubes 158 and into lumen 117. In some aspects, upon connecting link 157 with proximal ends of the first and second plungers (e.g., flanges 156, 159), distally moving at least one of rods 155, 160 can cause constituents of system 100 to be delivered through the first and second ports 138, mixed together within the mixing lumen 117 to form the gel composition and be delivered to the treatment site through the needle. Lumen 117 can include a static mixer so that constituent(s) from respective lumens 127, 129 can mix together and form the mixture of filler 30 (e.g., a gel composition) to be delivered through needle 108 to the treatment site.

Figures 4A, 4B, 4C, 4D:
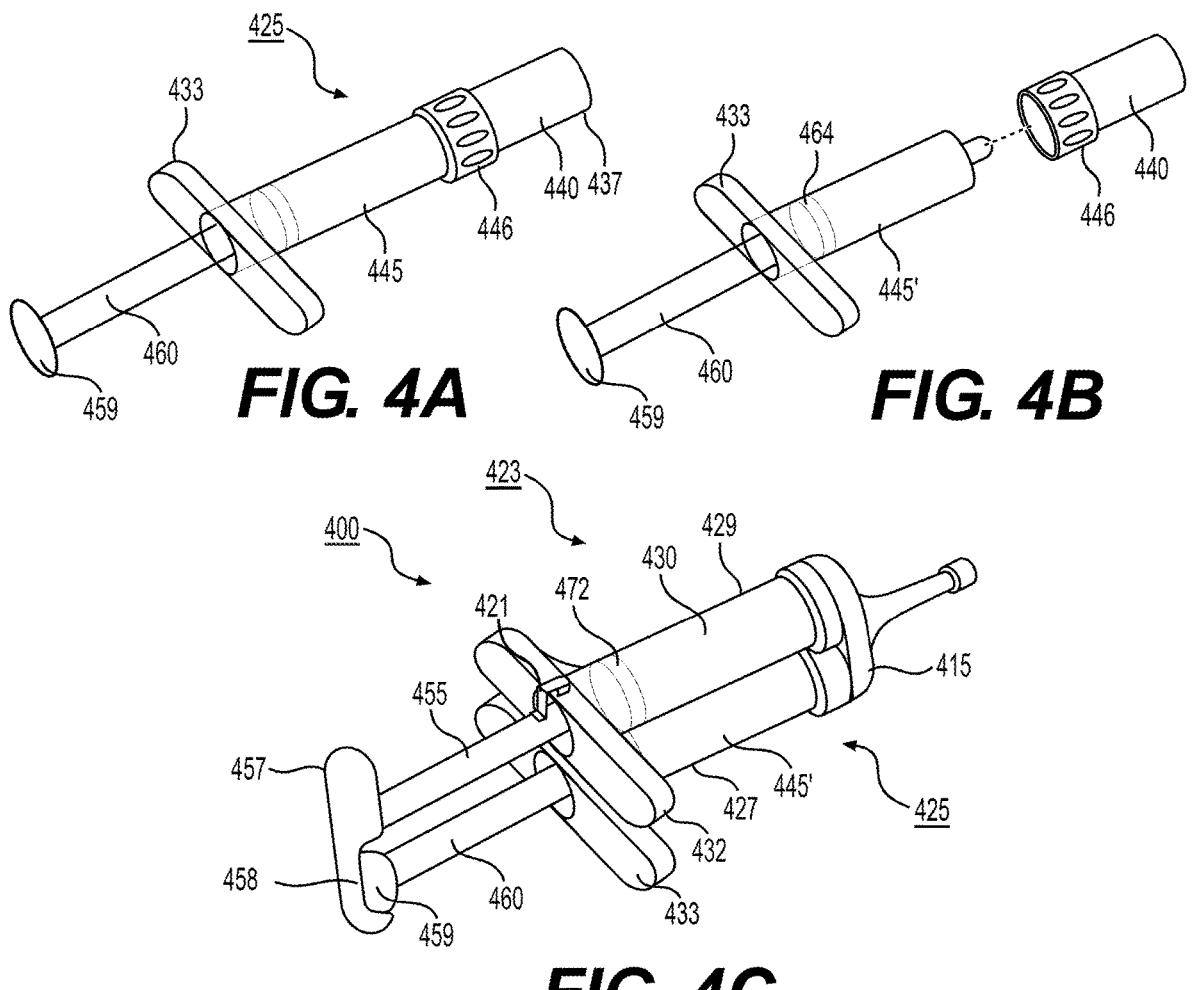
FIG. 4A depicts a partial upper perspective view of aspects of an example mixing system, in accordance with certain aspects of the present disclosure.
FIG. 4B depicts a partial upper perspective view of aspects of the example mixing system of FIG. 4A, in accordance with certain aspects of the present disclosure.
FIG. 4C depicts a partial upper perspective view of aspects of the example mixing system of FIG. 4A-4B, in accordance with certain aspects of the present disclosure.
FIG. 4D depicts a partial upper perspective view of aspects of the example mixing system of FIG. 4A-4C, in accordance with certain aspects of the present disclosure.

Turning to FIGS. 4A-4D, another exemplary mixing system 400 is shown in accordance with certain aspects of the present disclosure for mixing the mixture for use as filler 30. In FIG. 4A, a preloaded syringe 425 is provided with constituent 445 (e.g., diluent). Syringe 425 can include a rotatable knob 446 that is coupled to vial 437. Vial 437 can include constituent 440 (e.g., PEG). Syringe 425 as shown in FIG. 4A can inject constituent 445 through knob 446 and into vial 437. Once delivered, constituents 440, 445 can be shaken or otherwise mixed together to form precursor 445'. Once mixed, precursor 445' can be aspirated back to syringe 425 and knob 446 can be used to detach vial 437 therefrom, as shown in FIG. 4B. In FIG. 4C, syringe 425 is now assembled with second syringe 423. Lock 421 can be provided to lock rod 455 in position. Lock 421 can be removably connected to flange 432 of syringe 423 and bias into or otherwise couple to rod 455 so as to prevent its movement.

Syringe 423 includes a flange link 457. Rather than single flange link 157 as in system 100, flange link 457 is positioned at a proximal end of rod 455 and configured so that rotating rod 455 causes a receiver 458 formed with flange link 457 to contact and securely engage with flange 459 of syringe 425. For example, receiver 458 can include a recess formed in flange 457 configured to snuggle receive flange 459. In some aspects, receiver 458 can include a gap or space formed by upper and lower surfaces and flange 459 can be slidably engaged in the gap or the space in a sandwich configuration. In other aspects, the gap or space can be formed by flange 459 and receiver 458 can be slidably engaged in the gap or space of flange 459. However, receiver 458 is not so limited and can include a magnetic receiver to couple with magnetic coupler of flange 457. Receiver 458 and flange 459 can also couple by a snap-fit coupling engagement, a latch engagement, hook-and-loop fasteners or the like. FIG. 4D shows a lower perspective view of rod 455 and corresponding flange link 457.

Turning to FIGS. 5A-5F, another exemplary mixing system 500 is shown in accordance with certain aspects of the present disclosure for mixing a gel composition for use as filler 30. System 500 includes syringes 523, 525 that can each removably connected to connector 515. Connector 515 can include mixing lumen 517 extending from tubes 562 and corresponding lumens capable of removably connecting to ports 538 of respective syringes 523, 525. Connector 515 can form a Y-shape, though other shapes are contemplated as needed or required. Tubes 562 can be configured to pierce a seal or membrane of corresponding ports 538 when coupling syringes 523, 525 thereto.

Syringe 523 is similar to syringe 123. An exploded perspective view of syringe 525 is provided in FIG. 5B. As can be seen, rod 560 is provided with flange 559, whereby rod 560 includes plunger stopper 564 slidably inserted within proximal barrel portion 527a. Portion 527a can include a distal tip 524 configured to be inserted with an inner surface of a distal end of corresponding distal portion 527b. Fluid chamber 523a can be provided at or adjacent the distal tip 524. Chamber 523a can be concentric with portion 527a and include a diameter greater than an outer diameter of portion 527a. As can be seen, portion 527b can be similarly shaped so that its inner surface is shaped to receive an outer surface of chamber 523a in a correspondingly shaped inner surface of chamber 523b. A septum line 576 can be provided along an inner surface of chamber 523b at or adjacent a distal end of chamber 523b. In certain aspects, septum 576 can provide a seal between chambers 523a, 523b.

Figure 5A:
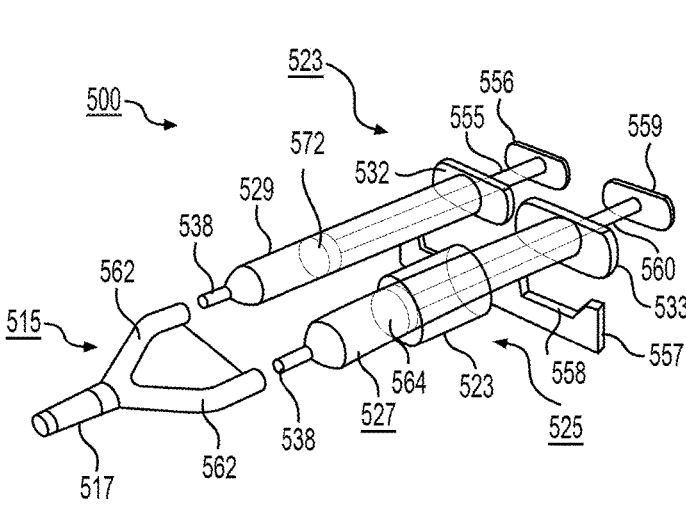
FIG. 5A depicts an exploded perspective view of aspects of an example mixing system, in accordance with certain aspects of the present disclosure.
Figure 5B:
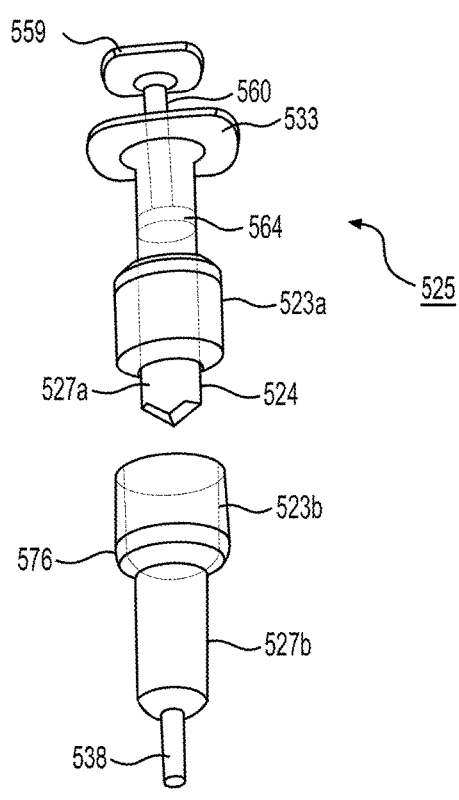
FIG. 5B depicts an exploded perspective view of aspects of the example mixing system of FIG. 5A, in accordance with certain aspects of the present disclosure.
Figure 5C:
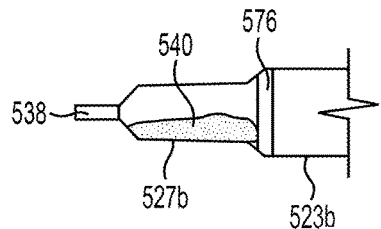
FIG. 5C depicts a partial side view of aspects of the example mixing system of FIGS. 5A-5B, in accordance with certain aspects of the present disclosure.
Figure 5D:
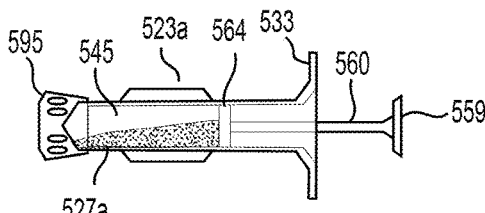
FIG. 5D depicts a partial side view of aspects of the example mixing system of FIGS. 5A-5C, in accordance with certain aspects of the present disclosure.
Figure 5E:
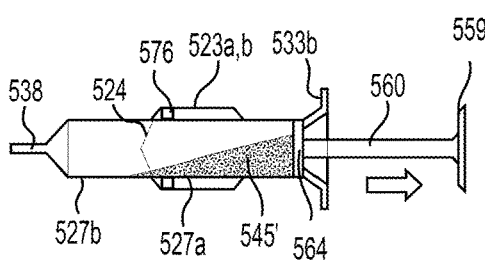
FIG. 5E depicts a partial side view of aspects of the example mixing system of FIGS. 5A-5D, in accordance with certain aspects of the present disclosure.
Figure 5F:
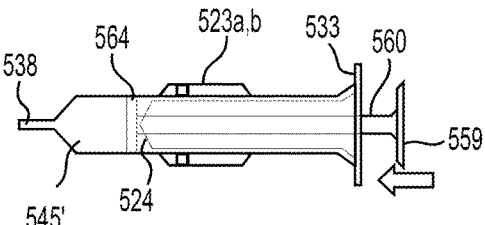
FIG. 5F depicts a partial side view of aspects of the example mixing system of FIGS. 5A-5E, in accordance with certain aspects of the present disclosure.

In FIG. 5C a partial, side cross-section view is shown of portion 527b is shown. Portion 527b can include constituent 540 (e.g., PEG). In FIG. 5D, a partial side view of proximal portion 527a of syringe 525 is provided in a portable state with cap 595. Portion 527a can include constituent 545. To couple portion 527a to portion 527b in order to form syringe 525, cap 595 can be removed to expose tip 524, which can be a one-way valve. With cap 595 removed in FIG. 5E, portions 527a, 527b can be coupled together by advancing tip 524 within portion 527b until chambers 523a, 523b are aligned. In some examples, an outer surface of tip 524 can include threads configured to engage with corresponding threaded receivers of portion 527b. Precursor 545' can be formed by advancing constituent 545 from portion 527a through tip 524 and into portion 527b, and contained therein by septum 576 so as to intermix with constituent 540. With precursor 545' formed, syringes 523, 525 can be assembled together as shown in FIG. 5A, and linked together by link 557. Link 557 can be functionally and structurally similar to link 457, so that link 557 can couple each of syringes 523, 525 together. For example, link 557 can include a receiver 558, similar to receiver 458, which can couple to respective flanges 532, 533 or any shaft or outer surface proximate thereof so as to couple syringes 523, 525 together. Once linked and assembled, fluids from syringes 523, 525 can be delivered to connector 515 to mix, form the mixture of filler 30, and ultimately delivered via a needle to the treatment site. System 500 is advantageous as syringe 525 is essentially split into two halves that can securely engage with each other and assembled easily with syringe 523.

Figure 6:
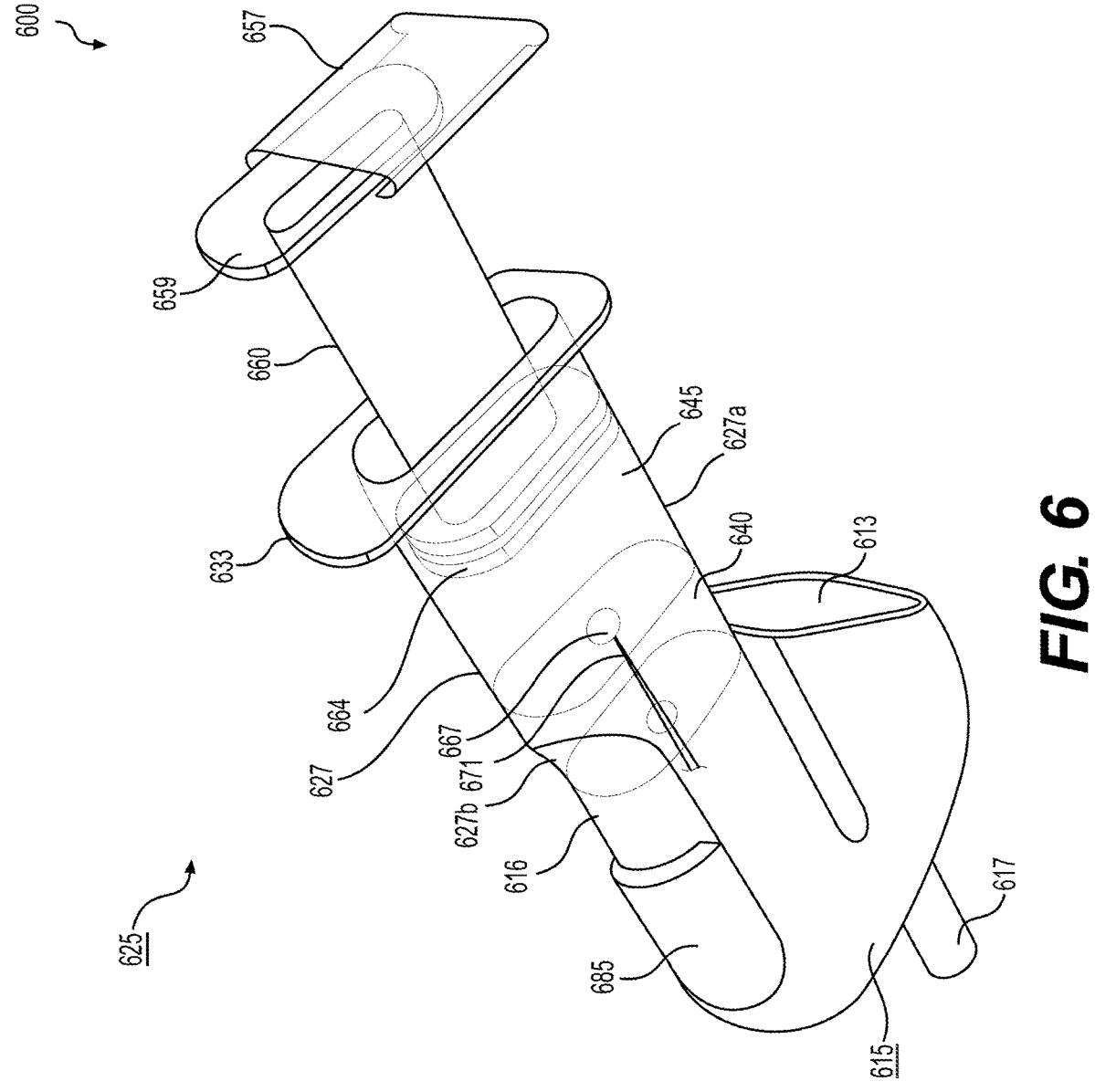
FIG. 6 depicts a perspective view of aspects of a syringe for use with an example mixing system, in accordance with certain aspects of the present disclosure.

Turning to FIG. 6, an exemplary syringe 625 is shown for use with a mixing system 600. Lumen 627 of syringe 625 can be divided into proximal chamber 627a and distal chamber 627b. Chamber 627a can include constituent 645 (e.g., diluent) and chamber 627b can include constituent 640 (e.g., PEG). Chambers 627a, 627b can be divided by divider 667. Divider 667 can include a sealed membrane that can provide a fluid path between chambers 627a, 627b. Divider 667 can be opened by moving rod 660 so as to mix constituents 640, 645 together and form precursor 645'.

In some aspects, divider 667 can be opened by sliding slider 685 to urge piercer 671 (e.g., a needle) to pierce divider 667 so constituent 645 can flow from 627a and into chamber 627b. In some examples, piercer 671 can include a sharpened tip or can include other shapes, such as a cross-shaped profile so as to create an opening in the membrane of divider 667 so as to quickly empty constituent 645 of chamber 627a without piercer 671 itself blocking the opening. Slider 685 as shown in is positioned on an outer surface of connector 615 and can be mechanically attached to piercer 671 so that movement from slider 685 can cause divider 667 to be opened. Slider 685 can be positioned elsewhere, including but not limited to adjacent at least one of chambers 627a, 627b.

Connector 615 can include portion 616 to receive syringe 625 and portion 613 to receive syringe 623 (not shown) aligned therewith. Connector 615 can include a mixing lumen 617 to couple with a needle. Link 657 is also provided so that when syringe 623 is assembled with portion 613, flange 656 can be mechanically linked with flange 659. Link 657 can include openings on either side configured to slide over and couple with flanges 659 and 656 (of syringe 623).

Figure 7:
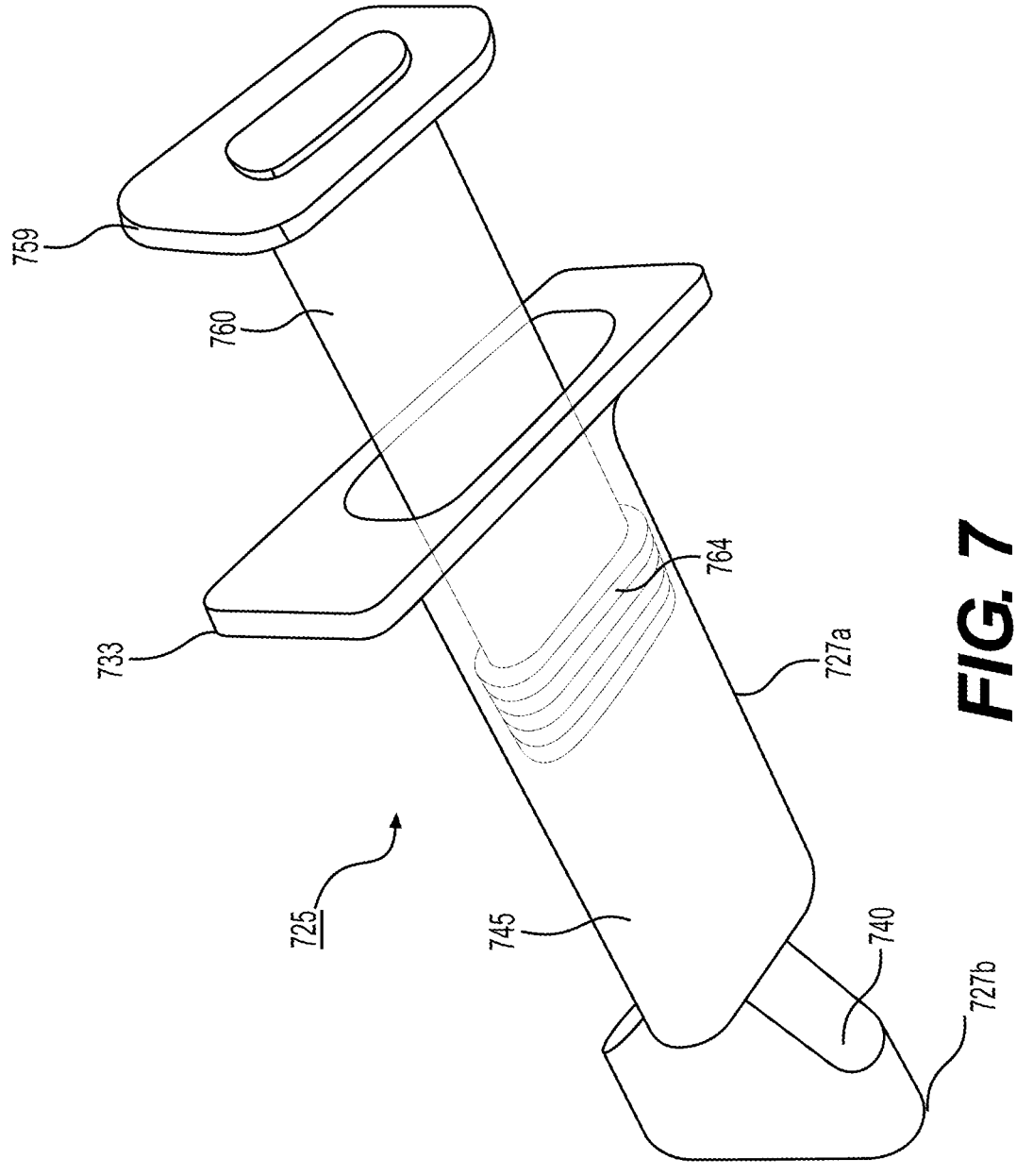
FIG. 7 depicts a perspective view of aspects of a syringe for use with an example mixing system, in accordance with certain aspects of the present disclosure.

Turning to FIG. 7, an exemplary syringe 725 is shown for use with a similar connector 615 for assembly with portion 616. Here, syringe 725 can include chambers 727a, 727b. Chamber 727a can include constituent 745 (e.g., diluent) while chamber 727b can include constituent 740 (e.g., PEG). Chamber 727b can be twisted or rotated as a regulator knob or valve. As a result, depending on the orientation, chambers 727b and 727a can be in fluid communication when open and have flow blocked when closed. As illustrated, chamber 727b is orthogonal relative to chamber 727a indicating a closed position. However, a user can rotate chamber 727b in either direction until chamber 727a is aligned parallel with chamber 727b indicating an open flow position. Once open, constituents 740, 745 can intermix to form precursor 745' and then be assembled with syringe 723 (not shown but similar in structure and function to herein disclosed syringes 623, 423, 123) to form system 700 via a connector similar to connector 615, as discussed above.

Figure 8:
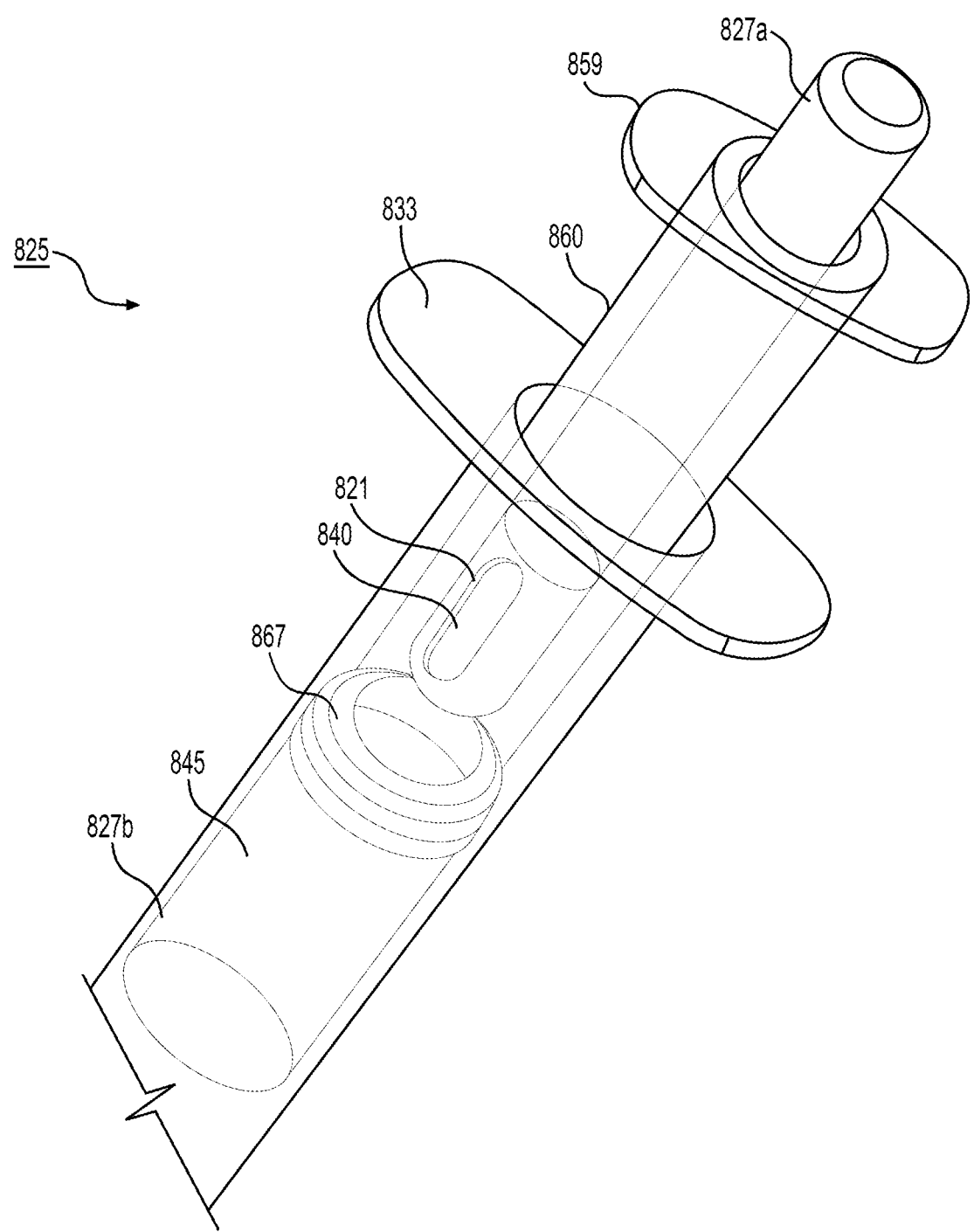
FIG. 8 depicts a perspective view of aspects of a syringe for use with an example mixing system, in accordance with certain aspects of the present disclosure.

Turning to FIG. 8, an exemplary syringe 825 is shown for use with a similar connector 615 for assembly with portion 616. Here, syringe 825 can include chambers 827a, 827b. Chamber 827a can include constituent 840 (e.g., PEG) while chamber 827b can include constituent 845 (e.g., diluent). Chamber 827a can be substantially elongate and/or cylindrical and insertable through an open, upper end of syringe 825 through an opening of plunger rod 860 at or adjacent flange 859. Rod 860 can be substantially allowed and in this respect, chamber 827a can be packaged separate from chamber 827b and be configured to partially extend out from rod 860 and flange 859 prior to mixing. Chamber 827b can be similarly elongate and/or cylindrical and include an inner diameter greater than an outer diameter of chamber 827a. When assembled, chambers 827a, 827b can be at least partially concentric with each other. Chamber 827a can be inserted into chamber 827b to effect mixing of constituents 840, 845. A septum 867 can separate chambers 827a, 827b.

In some aspects, mixing of constituents 840, 845 can be initiated by advancing, from a partially extended proximal end of chamber 827a, chamber 827a distally passed septum 867 so that once opening 821 is distal of septum 867, constituent 840 can egress and intermix with constituent 845 in chamber 827b to form precursor 845'. In certain aspects, constituent 840 can be prevented from flowing from opening 821 prior to being distal of septum 867 since opening 821 by being snugly sealed against an inner diameter of rod 860.

Once distal of septum 867, constituent 840 may no longer be sealed by the inner diameter of rod 860 can flow freely into chamber 827*b*. Opening 821 in some aspects can include an openable barrier, such as a one-way valve. Once precursor 845' is formed, syringe 825 can assemble with syringe 823 (not shown) to form system 800 via a connector 815 similar to connector 615.

Figures 9A, 9B, 9C, 9D, 9E:
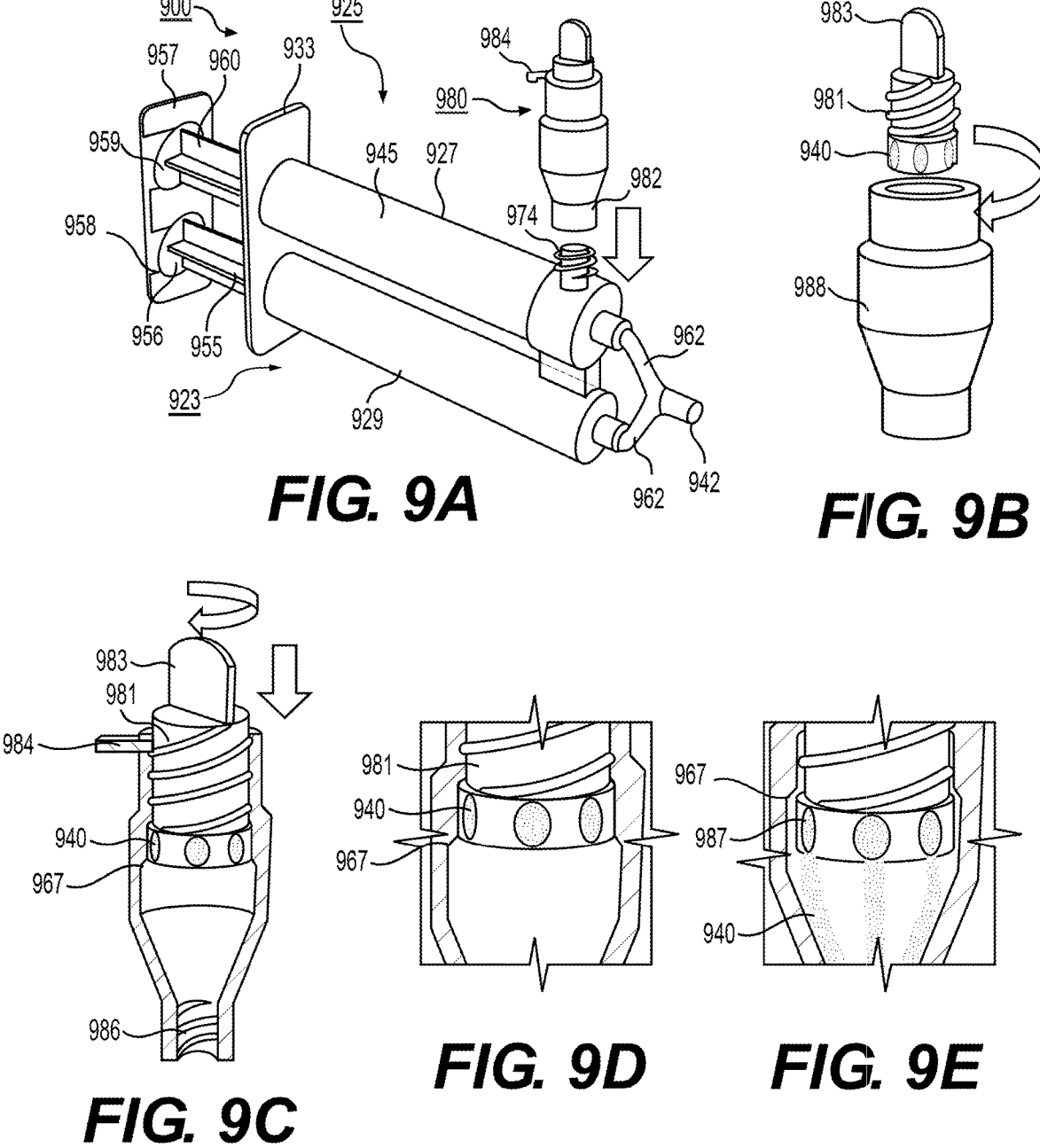
FIG. 9A depicts an exploded perspective view of aspects of an example mixing system, in accordance with certain aspects of the present disclosure.
FIG. 9B depicts an exploded perspective view of aspects of the example mixing system of FIG. 9A, in accordance with certain aspects of the present disclosure.
FIG. 9C depicts a partial side view of aspects of the example mixing system of FIGS. 9A-9B, in accordance with certain aspects of the present disclosure.
FIG. 9D depicts a partial side view of aspects of the example mixing system of FIGS. 9A-9C, in accordance with certain aspects of the present disclosure.
FIG. 9E depicts a partial side view of aspects of the example mixing system of FIGS. 9A-9D, in accordance with certain aspects of the present disclosure.

Turning to FIGS. 9A-9E, another exemplary mixing system 900 is shown in accordance with certain aspects of the present disclosure for mixing a mixture (e.g., a gel composition) for use as filler 30. System 900 is shown in FIG. 9A in an exploded view with vial 980 being assembled with the rest of system 900. System 900 includes syringes 923, 925 that can be mechanically linked at respective flanges 956, 959 via link 957, similar to links 157, 457, 657, attendant with corresponding receivers 958 of link 958. Syringe 923 can be structurally similar to those of system 100, including lumen 129, rod 155, flange 156, port 138 and the like. Portion 927 can include constituent 945 therein (e.g., diluent) while portion 929 can include constituent 930 (e.g., accelerant).

Vial 980 can be connected to a port 974 of portion 927 so as to deliver constituent 940 (e.g., PEG) to portion 927 to form precursor 945'. Vial 988 can include a lower luer fitting 982 coupled with a larger lumen 988 that can receive housing 981. Housing 981 can include constituent 940. While not shown, port 974 can include a cap that is detachable between uses of vial 980. Vial 980 can include a luer fitting 982 to couple to port 974.

Once coupled to lumen 927 and desired for use, a tamper resistant seal 984 can be removed from vial 980 and actuator 983 can be rotated to cause constituent 940 to be released through internal openings 987 of housing 981, into lumen 988 and through port 974. The process of releasing constituent 940 from housing 981 is shown between FIGS. 9C and 9E when actuator 983 is rotated causing constituent 940 in housing 981 to release through openings 987. In certain aspects, constituent 940 can be prevented from flowing through openings 987 prior to being distal of increased internal diameter 967 of lumen 988 since openings 987 can snugly seal against internal diameter 967. Once distal of internal diameter 967 (e.g., by being inserted or threadingly advanced into lumen 988), constituent 940 may no longer be sealed by the internal diameter and can flow freely from housing 981. Once precursor 945' is formed by mixing constituent 940 with constituent 945 of lumen 927, flanges 956, 955 can be linked via link 957 and rods 955, 960 can be distally advanced to produce the mixture for filler 30 (e.g., gel composition) in connector 915.

Turning to FIGS. 10A-10E, another exemplary mixing system 1000 is shown in accordance with certain aspects of the present disclosure for producing a mixture (e.g., a gel composition) for use as filler 30. System 1000 is shown in FIG. 10A in an upper, perspective view with rods 1060, 1055 withdrawn. Constituent 1030 (e.g., accelerant) can be stored in lumen 1029 and controlled by rod 1055 and corresponding stopper 1072, similar to previous mixing systems of this disclosure. Lumen 1027 can be divided into a distal portion 1027*b* which can house constituent 1045 (e.g., diluent) and a proximal portion 1027*a* which can house constituent 1040 (e.g., PEG). Portion 1027*a* can be formed with and proximal of piston stopper 1064, as shown more clearly in FIG. 10B, whereby stopper 1064 can include an internal cavity housing constituent 1040.

FIG. 10B is a side, cross-section view showing stopper 1064 including a valve 1069 openable by rotating knob 1046. Rod 1060 can be formed by inner rod 1060*b* inserted within outer rod 1060*a*. Outer rod 1060*a* can be rotatably coupled to knob 1046 and controlled by flange 1057. In some aspects, inner rod 1060*b* can also be rotatably coupled to and controlled by knob 1046. Rod 1060*b* can be in contact with valve 1069 at its distal tip. In some aspects, rotating knob 1046 can cause knob 1046 to advance proximally or distally along an outer surface of rod 1060*a*. In turn, rotating knob 1046 can cause rod 1060*b* to move proximally thereby opening a window of valve 1069 so constituents 1040, 1045 can intermix to form precursor 1045'. FIG. 10C shows a partial, perspective view illustrating user U actuating knob 1046 so constituents 1040, 1045 can intermix to form precursor 1045'. Here, outer markings 1051 are aligned on knob 1046 and rod 1060 indicating that valve 1069 is open. If markings 1051 are misaligned, then valve 1069 can be understood as closed. FIG. 10D shows a partial, close-up perspective view of an optional cap 1095*a* on needle adaptor 1095*b* distally connected to lumen 1027, 1029. Cap 1095 can include one or more openings to purge excess fluid or unwanted air from system. Cap 1095 can also be removed entirely from system, as shown in FIG. 10E, where lumen 1007 can remain in the absence of cap 1095 so that needle 1008 can be attached thereon. It is contemplated that system 1000 can also include a Y-shaped connector or any other connector of this disclosure to facilitate coupling with needle, in addition to or in place of cap 1095 and lumen 1007.

Figures 11A, 11B, 11C, 11D, 11E, 11F, 11G, 11H:
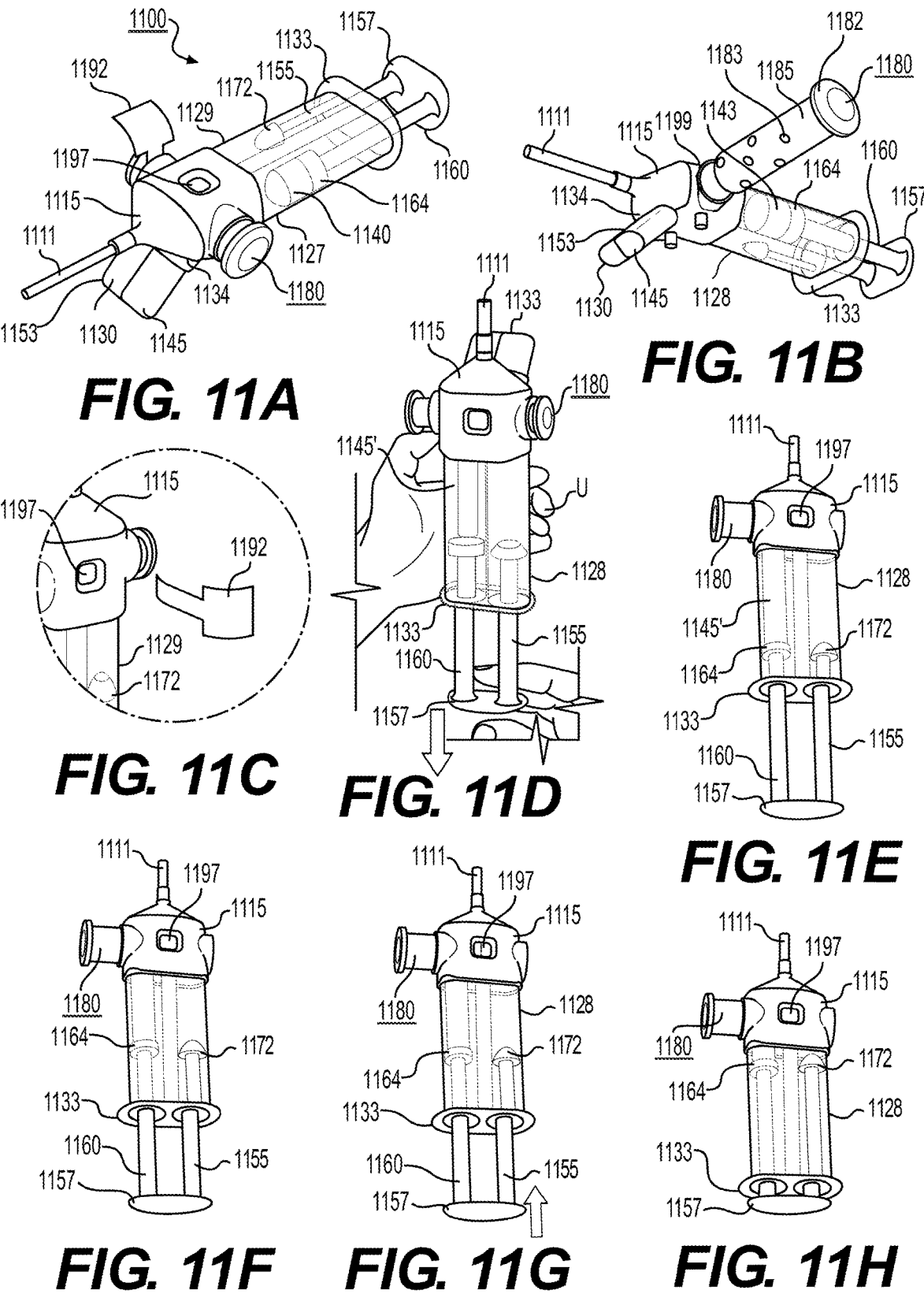
FIG. 11A depicts a perspective view of aspects of an example mixing system, in accordance with certain aspects of the present disclosure.
FIG. 11B depicts a partial side, cross-sectional view of aspects of the example mixing system of FIG. 11A, in accordance with certain aspects of the present disclosure.
FIG. 11C depicts a partial side, cross-sectional view of aspects of the example mixing system of FIGS. 11A-11B, in accordance with certain aspects of the present disclosure.
FIG. 11D depicts a perspective view of aspects of the example mixing system of FIGS. 11A-11C, in accordance with certain aspects of the present disclosure.
FIG. 11E depicts a close-up, partial perspective view of aspects of the example mixing system of FIGS. 11A-11D, in accordance with certain aspects of the present disclosure.
FIG. 11F depicts a close-up, partial perspective view of aspects of the example mixing system of FIGS. 11A-11E, in accordance with certain aspects of the present disclosure.
FIG. 11G depicts a close-up, partial perspective view of aspects of the example mixing system of FIGS. 11A-11F, in accordance with certain aspects of the present disclosure.
FIG. 11H depicts a close-up, partial perspective view of aspects of the example mixing system of FIGS. 11A-11G, in accordance with certain aspects of the present disclosure.

Turning to FIGS. 11A-11H, another exemplary mixing system 1100 is shown in accordance with certain aspects of the present disclosure for mixing a mixture for use as filler 30. System 1100 is shown in FIG. 11A in an upper, perspective view with rods 1160, 1155 partially withdrawn from receiver 1128. A fluid container 1153 can be detachably connected to a distal end of system 1100 (e.g., at connector 1115). Container 1153 can be a vial that can include constituent 1130 (e.g., accelerant) in a first chamber configured to connect with lumen 1129 (e.g., via port 1138). Container 1153 can include constituent 1145 (e.g., diluent) in a second chamber configured to connect with another port 1138 that can be in fluid communication with lumen 1129. Once container 1153 is connected to system 1100, container 1153 can be configured to deliver constituents 1130, 1145 to lumens 1129, 1127, respectively. Lumen 1127 can include constituent 1140 (e.g., PEG) which can be positioned at or adjacent stopper 1164.

In some aspects, connector 1115 can include a hole 1199 extended through connector 1115 and/or orthogonal to lumens 1127, 1129. Hole 1199 can be sized to receive an insert 1180. Insert 1180 can be substantially cylindrical and shaped to be inserted through hole 1199. In some aspects, insert 1180 can be shaped in a flute-like manner with a plurality of channels 1183 selectively positioned from an outer surface through insert 1180. In some aspects, rotating and/or sliding insert 1180 with respect to hole 1199 and connector 1115 can control or adjust fluid flow within the mixing lumen 1117 of connector 1115 and/or flow in and out of lumens 1127, 1229. In some aspects, connector can include a display 1197 that indicates a flow status of the system defined by an orientation and/or position of insert 1180 with respect to lumen 1117 and hole 1199. For example, display 1197 can indicate closed or open depending on insert 1180. Display 1197 can also include color settings (e.g., red being closed or green being open). Display 1197 can also include a numeric identifier indicating strength of flow (e.g., 1, 2, 3, 4, 5, etc.). System 1100 can include locking mechanism 1192 removably connected to insert 1180. Mechanism 1192 can be configured to mechanically prevent insert 1180 from being removed or otherwise adjusted so as to lock insert 1180 in position. Mechanism 1192 can include a latch or pin configured to be inserted into a distal or proximal end of insert 1180 so as to prevent movement of insert 1180 from hole 1199.

FIGS. 11B to 11H show a process of using system 1100. In FIG. 11B, insert 1180 is shown exploded, prior to being assembled in hole 1199. Container 1153 is attached to fluid port 1134 of connector 1115. Rods 1155, 1160 are partially withdrawn from respective lumens 1129, 1127, respectively. In FIG. 11C, locking mechanism 1192 is being removed from insert 1180. With mechanism 1192 removed, in FIG. 11D insert 1180 has been slid into hole 1199 to a first position. In the first position, container 1153 is in fluid communication with lumens 1127, 1129. The first state can be indicated in display 1197.

With fluid communication established, rods 1155, 1160 are withdrawn causing constituents 1130, 1145 to be aspirated from container 1153 into lumens 1129, 1127, respectively. In FIG. 11E, precursor 1145' has been formed in lumen 1127 by introducing constituent 1145 and mixing it with constituent 1140. In some aspects, this is seen moving from FIGS. 11D to 11E as flange 1157 is urged proximally, as denoted by the proximal arrow of FIG. 11D. With precursor 1145' formed, insert 1180 has been further drawn through hole 1199 to a second position, as denoted by the outward arrow. The second position can be indicated in display 1197, as indicated with the exemplary change in status indicator "!" shown in FIG. 11G. The second position of insert 1180 can permit flow from lumens 1127, 1129 through connector 1115 and into needle adaptor 1111. Between FIGS. 11G and 11H, rods 1155, 1160 are advanced distally, as denoted by the distally oriented arrow of FIG. 11G, so that stoppers 1172, 1164 advance constituents of respective lumens 1129, 1127 through connector 1115 and into needle adaptor 1111 to form the gel composition of filler 30. It is contemplated that insert 1180 can be moved and/or otherwise adjusted in a variety of different configurations (e.g., fewer or greater than the two positions of the depicted example).

FIG. 12 depicts a method 1200 of using any of the herein disclosed mixing systems. Step 1210 of method 1200 can include opening, by the first plunger, a barrier between proximal and distal portions within the first lumen thereby mixing the first constituent with another constituent in a first state to form a first mixture. Step 1220 of method 1200 can include moving the second plunger causing the first constituent and the second constituent to be delivered through the first and second ports and mixed together within the mixing lumen to form the mixture. Method 1200 can end after step 1220. In other embodiments, additional steps according to the examples described above can be performed.

The systems and methods of this disclosure are beneficial by reducing the number of system components, are relatively simply to assemble and operate, with minimal mixing errors prior to delivery within a patient at a treatment site. Other aspects and embodiments of the present disclosure will be apparent to those skilled in the art from consideration of the specification and practice of the embodiments disclosed herein.

While certain features of the present disclosure are discussed within the context of exemplary procedures, the compositions, systems, and methods may be used for other medical procedures according to the general principles disclosed. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein. It is intended that the specification and examples be considered as exemplary only, with a true scope and spirit of the present disclosure being indicated by the following claims.

What is claimed is:

1. A system for producing a mixture to deliver to a treatment site, comprising:
   a mixing lumen attachable to a proximal end of a delivery system;
   a multi-lumen chamber removably connected to and in fluid communication with a proximal end of the mixing lumen and comprising a first lumen aligned with a second lumen;
   the first lumen configured to comprise a first constituent in a first cavity that terminates in a first port in fluid communication with the proximal end of the mixing lumen, a first rod coupled to a first plunger internally positioned within the first lumen; and
   the second lumen configured to comprise a second constituent, a second plunger internally positioned within the second lumen, the second lumen terminating in a second port adjacent the first port and in fluid communication with the proximal end of the mixing lumen;
   wherein the first rod comprises a knob and the first plunger comprises an internal cavity comprising a third constituent, and wherein rotating the knob causes the third constituent to be released from the internal cavity and mix with the first constituent to form a first mixture; and
   wherein distally moving the second plunger causes the first mixture and the second constituent to be delivered through the first and second ports and mixed together within the mixing lumen to form the mixture.

2. The system of claim 1, wherein the mixing lumen is in a connector comprising a distal end and a proximal end, the distal end of the mixing lumen being attachable to a proximal end of a needle.

3. The system of claim 1, wherein the knob is between the first plunger and a flange of the first rod.

4. The system of claim 1, wherein the first constituent comprises a diluent and the third constituent comprises a hydrophilic polymer.

* * * * *